(12) United States Patent
Sarah

(10) Patent No.: US 10,118,869 B1
(45) Date of Patent: Nov. 6, 2018

(54) FERTILIZER

(71) Applicant: Anthony Sarah, Tucson, AZ (US)

(72) Inventor: Anthony Sarah, Tucson, AZ (US)

( * ) Notice: Subject to any disclaimer, the term of this patent is extended or adjusted under 35 U.S.C. 154(b) by 0 days.

(21) Appl. No.: 15/642,822

(22) Filed: Jul. 6, 2017

Related U.S. Application Data

(63) Continuation of application No. 15/431,314, filed on Feb. 13, 2017, now abandoned.

(51) Int. Cl.
| | |
|---|---|
| *C05F 3/02* | (2006.01) |
| *C05G 3/00* | (2006.01) |
| *C05G 3/04* | (2006.01) |
| *C05G 3/02* | (2006.01) |
| *A01N 65/26* | (2009.01) |
| *C05B 17/00* | (2006.01) |
| *C05D 1/04* | (2006.01) |
| *C05D 1/00* | (2006.01) |
| *A01N 43/38* | (2006.01) |

(52) U.S. Cl.
CPC ............... *C05G 3/02* (2013.01); *A01N 43/38* (2013.01); *A01N 65/26* (2013.01); *C05B 17/00* (2013.01); *C05D 1/00* (2013.01); *C05D 1/04* (2013.01); *C05F 3/02* (2013.01); *C05G 3/00* (2013.01); *C05G 3/04* (2013.01)

(58) Field of Classification Search
None
See application file for complete search history.

(56) References Cited

U.S. PATENT DOCUMENTS

| | | | | |
|---|---|---|---|---|
| 6,596,324 | B1 * | 7/2003 | Homan | A01N 25/08 424/761 |
| 2013/0133386 | A1 * | 5/2013 | Baker | C05F 17/02 71/10 |
| 2013/0145805 | A1 * | 6/2013 | Olson | C05D 9/00 71/6 |
| 2015/0299061 | A1 * | 10/2015 | Catto | C05C 9/005 504/241 |
| 2016/0355445 | A1 * | 12/2016 | Bobeck | C05F 11/08 |
| 2017/0283337 | A1 * | 10/2017 | Gaunt | C05F 17/0036 |

FOREIGN PATENT DOCUMENTS

| | | | |
|---|---|---|---|
| ID | 37773 | * | 7/2011 |
| JP | 2004026568 | * | 1/2004 |
| WO | 2011/070586 | * | 6/2011 |

OTHER PUBLICATIONS

U.S. Appl. No. 62/322,586, filed Apr. 14, 2016.*

* cited by examiner

*Primary Examiner* — Wayne A Langel
(74) *Attorney, Agent, or Firm* — Etherton Law Group, LLC

(57) ABSTRACT

This fertilizer is a mixture of organic matter from animal and plant sources, nematode controllers, carbohydrates, minerals, and mycorrhizal inoculum. It contains guano, kelp meal, neem cake, dry molasses, clay, magnesium sulfate and mycorrhizae. In one embodiment, the mixture is made of the following amounts by weight: 55% high-nitrogen bat guano; 12.5% high-phosphorous bat guano; 12.5% kelp meal; 10% neem cake; and 2.5% each of dry molasses, montmorillonite clay, magnesium sulfate, and mycorrhizae of the *Glomus* genus. Versions of the fertilizer directed to specific plant species may contain additional ingredients, such as indole-3-butyric acid.

3 Claims, No Drawings

FERTILIZER

CROSS-REFERENCE TO RELATED APPLICATIONS

This application is a continuation of co-pending U.S. application Ser. No. 15/431,314 filed Feb. 13, 2017.

FIELD OF INVENTION

This invention relates generally to a fertilizer for plants. This invention relates more specifically to a fertilizer made with bat guano, kelp meal, neem cake and other ingredients that causes fast plant growth and improved freeze protection.

BACKGROUND

Fertilizers have been used for millennia to enhance the growth of plants. Fertilizers can affect the plant's rate of growth; its hardiness in the face of high and low temperatures, insects, fungus and bacteria; soil alkalinity, soil moisture, and other factors affecting growth. The components of the fertilizer and their proportions change the effectiveness of a fertilizer.

Fertilizers typically contain macronutrients nitrogen, phosphorus and potassium, and micronutrients such as minerals and metals. The source of the nutrients can be from animal matter, plant matter, or synthetic ingredients formed by chemical reactions. Both organic (carbon-containing molecules from animals or plants) and inorganic ingredients can be found in fertilizers.

SUMMARY OF THE INVENTION

This fertilizer is a mixture of organic matter from animal and plant sources, nematode controllers, carbohydrates, minerals, and mycorrhizal inoculum. It contains guano, kelp meal, neem cake, dry molasses, clay, magnesium sulfate and mycorrhizae. In one embodiment, the mixture is made of the following amounts by weight: 55% high-nitrogen bat guano; 12.5% high-phosphorous bat guano; 12.5% kelp meal; 10% neem cake; and 2.5% each of dry molasses, montmorillonite clay, magnesium sulfate, and mycorrhizae of the *Glomus* genus. Versions of the fertilizer directed to specific plant species may contain additional ingredients, such as indole-3-butyric acid.

DETAILED DESCRIPTION OF THE INVENTION

This fertilizer is a mixture of guano, kelp meal, neem cake, dry molasses, clay, magnesium sulfate and mycorrhizae. The combination encourages fast plant growth and improved freeze protection. It is particularly useful for fertilizing *cannabis* plants.

Guano supplies nitrogen, phosphorous and some potassium in the fertilizer, and is the largest single ingredient of the mixture by weight. The amount of guano used in the mixture ranges from about 40-90% by weight and is typically about 65% by weight. In one embodiment the guano is bat guano and is preferably divided between high-nitrogen bat guano having a nitrogen-phosphorous-potassium percentages ("NPK") of 9-3-1 and high-phosphorous bat guano having an NPK of 0-10-1. Bat guano is high in organic materials, retains moisture well, acts to control nematodes and insects, acts as a fungicide and has microbes to help neutralize toxins in the soil. In the preferred embodiment, 55% of the mixture by weight is high-nitrogen bat guano and 12.5% of the mixture by weight is high-phosphorous bat guano, for a total of 67.5% bat guano by weight. In another embodiment the guano is 50-55% bat guano and 10-15% poultry guano, also known as chicken manure, which has a relatively high concentration of nitrogen, phosphorous, and potassium. Poultry manure has an NPK of 10-2-3. In another embodiment the guano is 50-55% bat guano and 10-15% sea bird guano, which has a relatively high concentration of nitrogen and phosphorous, but relatively little potassium. The amount of each type of guano can be changed to vary the concentration of nitrogen and phosphorus as desired.

Kelp meal is also known as sea kelp meal or seaweed meal. Although it supplies some nitrogen and phosphorous with a typical NPK of 1-0-2, the main contribution of kelp meal to the fertilizer is that it supplies potassium and other minerals, along with amino acids, vitamins and trace elements that enhance plant growth. Kelp meal is the second largest single ingredient by weight, typically 8-17% by weight. In the preferred embodiment the kelp meal is 12.5% of the mixture by weight.

Neem cake is the third largest single ingredient by weight, typically 6-14% by weight. Neem cake helps control parasitic nematodes at the roots and is an insecticide. Neem cake also beneficially increases earthworm activity and is a nitrification inhibitor to prolong the availability of nitrogen to plants. In the preferred embodiment, neem cake is 10% of the mixture by weight.

The mixture includes several other ingredients, typically in smaller proportions than the other ingredients. In the preferred embodiment, the mixture also comprises dry molasses, montmorillonite clay, magnesium sulfate, and mycorrhizae.

Dry molasses can be used in powder or granulated form, typically making up 1.5-3.5% of the mixture by weight. Dry molasses adds carbon in the form of carbohydrates to feed soil microorganisms. Molasses also contains sulphur, potash and a variety of micronutrients needed by plants. The N-P-K ratio of molasses is typically about 1-0-5. In the preferred embodiment the dry molasses is in powder form and is 2.5% of the mixture by weight.

Clay is used in powder form, typically making up 1.5-3.5% of the mixture by weight. Clays provide high mineral content including mineral silicates, calcium, copper, and zinc. Any clay may be used, but preferably in the preferred embodiment the clay is montmorillonite clay and is 2.5% of the mixture by weight.

Magnesium sulfate can be used in the anhydrous or hydrated forms, typically making up 1.5-3.5% of the mixture by weight. Organic (mined) or synthesized magnesium sulfate can be used. In the preferred embodiment, the organic, hydrated form of the salt is used, also known as Epsom Salt, and is 2.5% of the mixture by weight.

Mycorrhizae, also known as mycorrhizal inoculum, typically makes up 1.5-3.5% of the mixture by weight. Mycorrhizae colonize the plant root with fungus to help plants capture nutrients such as phosphorus, sulfur, nitrogen and micronutrients from the soil. In the preferred embodiment, the genus *Glomus intraradices*, also known as *Rhizophagus irregularis*, is used and is 2.5% of the mixture by weight.

Versions of the fertilizer directed to specific plant species may contain additional ingredients. For example, indole-3-butyric acid can be added for the mixture's use on cacti, and non-edible landscape trees and shrubs.

The mixture is applied initially by spreading it in the planting hole. During growing season the mixture is used to top dress the soil around the plants monthly at a rate of 10 lbs/100 sq. ft. Higher application rates may further speed plant growth.

Typically the fertilizer is made in batches by combining all ingredients in dry form. For a 20 lb batch, the ingredients are typically mixed by hand. For larger batches, the ingredients can be added to a garbage can and mixed using a commercial mixer with a wire whisk or egg-beater attachment. For commercial quantities the ingredients can be mixed in batches with dry bulk mixers or on a mixing pad with a front-end loader.

Example 1

The following ingredients are mixed by hand to make a 20 lb batch of the mixture:
a) 11 lbs high-nitrogen bat guano;
b) 2.5 lbs high-phosphorous bat guano;
c) 2.5 lbs kelp meal;
d) 2.0 lbs neem cake;
e) 0.5 lbs dry molasses powder;
f) 0.5 lbs montmorillonite clay;
g) 0.5 lbs hydrated magnesium sulfate; and
h) 0.5 lbs *Glomus intraradices* mycorrhizae.

Example 2

The following ingredients are mixed by hand to make a 20 lb batch of the mixture:
a) 10 lbs bat guano;
b) 3.5 lbs chicken manure;
c) 2.5 lbs kelp meal;
d) 2.0 lbs neem cake;
e) 0.5 lbs dry molasses powder
f) 0.5 lbs montmorillonite clay;
g) 0.5 lbs hydrated magnesium sulfate; and
h) 0.5 lbs *Glomus intraradices* mycorrhizae Example 3

The following ingredients are mixed by hand to make a 20 lb batch of the mixture:

a) 11 lbs bat guano;
b) 2.5 lbs seabird guano;
c) 2.5 lbs kelp meal;
d) 2.0 lbs neem cake;
e) 0.5 lbs dry molasses powder;
f) 0.5 lbs montmorillonite clay;
g) 0.5 lbs hydrated magnesium sulfate; and
h) 0.5 lbs *Glomus intraradices* mycorrhizae.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

I claim:
1. A dry fertilizer comprising:
a) bat guano in dry form 45-90% by weight;
b) kelp meal in dry form 8-16% by weight;
c) neem cake in dry form 6-13% by weight;
d) dry molasses 1.5-3.5% by weight;
e) montmorillonite clay in dry form 1.5-3.5% by weight;
f) magnesium sulfate in dry form 1.5-3.5% by weight; and
g) mycorrhizae inoculum in dry form 1.5-3.5% by weight.
2. A dry fertilizer consisting of:
a) bat guano in dry form 66-68% by weight;
b) kelp meal in dry form 12-13% by weight;
c) neem cake in dry form 9-11% by weight;
d) dry molasses in dry form 2-3% by weight;
e) montmorillonite clay in dry form 2-3% by weight;
f) magnesium sulfate in dry form 2-3% by weight; and
g) mycorrhizae inoculum in dry form 2-3% by weight.
3. A dry fertilizer consisting of:
a) bat guano in dry form 67.5% by weight;
b) kelp meal in dry form 12.5% by weight;
c) neem cake in dry form 10% by weight;
d) dry molasses 2.5% by weight;
e) montmorillonite clay in dry form 2.5% by weight;
f) magnesium sulfate in dry form 2.5% by weight; and
g) mycorrhizae inoculum in dry form 2.5% by weight.

* * * * *